United States Patent
Choi et al.

(10) Patent No.: US 11,602,552 B2
(45) Date of Patent: Mar. 14, 2023

(54) LACTOBACILLUS PLANTARUM KBL396 STRAIN AND USE THEREOF

(71) Applicant: KoBioLabs, Inc., Seoul (KR)

(72) Inventors: Yongbin Choi, Seoul (KR); Jisoo Kim, Seoul (KR); June-Chui Lee, Yangpyeong-gun (KR); Gwang Pyo Ko, Seoul (KR); Tae-Wook Nam, Seongnam-si (KR); Jun-Hyeong Kim, Suwon-si (KR); Bo-Ram Cho, Yongin-si (KR)

(73) Assignee: KOBIOLABS, INC., Seoul (KR)

( * ) Notice: Subject to any disclaimer, the term of this patent is extended or adjusted under 35 U.S.C. 154(b) by 16 days.

(21) Appl. No.: 16/962,976

(22) PCT Filed: Feb. 7, 2019

(86) PCT No.: PCT/KR2019/001525
§ 371 (c)(1),
(2) Date: Jul. 17, 2020

(87) PCT Pub. No.: WO2019/151843
PCT Pub. Date: Aug. 8, 2019

(65) Prior Publication Data
US 2022/0040243 A1  Feb. 10, 2022

(30) Foreign Application Priority Data
Feb. 2, 2018 (KR) .......................... 10-2018-0013366

(51) Int. Cl.
*A61K 35/747* (2015.01)
*A23K 10/18* (2016.01)
*A23L 33/135* (2016.01)

(52) U.S. Cl.
CPC ............ *A61K 35/747* (2013.01); *A23K 10/18* (2016.05); *A23L 33/135* (2016.08)

(58) Field of Classification Search
None
See application file for complete search history.

(56) References Cited

U.S. PATENT DOCUMENTS

2016/0067289 A1* 3/2016 Berggren ............... C12N 1/205
424/93.45
2017/0312232 A1 11/2017 Vitetta et al.

FOREIGN PATENT DOCUMENTS

EP       2528610       11/2013
JP    2012-017282       1/2012
(Continued)

OTHER PUBLICATIONS

Maciel, M.I.S. et al. "Prebiotics and Probiotics—Potential Benefits in Human Nutrition and Health", IntechOpen, Chapter2, pp. 1-15. (Year: 2020).*

(Continued)

*Primary Examiner* — Michelle F. Paguio Prising
*Assistant Examiner* — Grant C Gurrens
(74) *Attorney, Agent, or Firm* — Lex IP Meister, PLLC

(57) ABSTRACT

The present invention relates to a composition comprising at least one selected from the group consisting of a novel lactic acid bacterium, *Lactobacillus plantarum* KBL396 (KCTC13278BP), culture of the strain, lysate of the strain and extract of the strain, and its use for food and medicine. The strain and composition according to the present invention has an excellent effect on improvement of neurological diseases, particularly improvement of mental disorders and neurodegenerative diseases, and has no risk of side effects in a human body, and thus it can be usefully utilized as a use for improvement of neurological diseases.

6 Claims, 7 Drawing Sheets
Specification includes a Sequence Listing.

(56) References Cited

FOREIGN PATENT DOCUMENTS

| | | | |
|---|---|---|---|
| JP | 2015-213501 | 12/2015 | |
| JP | 2017222601 A | * 12/2017 | |
| KR | 10-1394348 | 5/2014 | |
| KR | 10-2015-0134824 | 12/2015 | |
| KR | 10-1620163 | 5/2016 | |
| RU | 2642301 | 1/2018 | |
| WO | 2009-027753 | 3/2009 | |
| WO | 2013-109635 | 7/2013 | |
| WO | WO-2016065419 A1 | * 5/2016 | ........... A61K 35/745 |
| WO | 2018-014225 | 1/2018 | |
| WO | 2020-171256 | 8/2020 | |

OTHER PUBLICATIONS

Maloteaux, J.M. et al. "Decrease of Serotonin-S2 Receptors in Temporal Cortex of Patients with Parkinson's Disease and Progressive Supranuclear Palsy", Movement Disorders. 3(3). pp. 255-262. (Year: 1988).*
Sarropoulou, V. "Serotonin and Melotonin—Their Functional Role in Plants, Food, Phytomedicine, and Human Health", CRC Press, Chapter 30, pp. 445-466. (Year: 2017).*
Lai, TJ et al. "Polymorphism screening and haplotype analysis of the tryptophan hydroxylase gene (TPH1) and association with bipolar affective disorder in Taiwan", BMC Medical Genetics, 6(14), pp. 1-10 (Year: 2005).*
Andreou, D. et al. "Polymorphisms in genes implicated in dopamine, serotonin and noradrenalin metabolism suggest association with cerebrospinal fluid monoamine metabolite concentrations in psychosis", Behavioral and Brain Functions. 10(26). pp. 1-10. (Year: 2014).*
Müller-Vahl, K.R. et al. "Serotonin transporter binding is increased in Tourette syndrome with Obsessive Compulsive Disorder", Scientific Reports. 9(972). pp. 1-10. (Year: 2019).*
Deryabina, I.B. et al. "Impairing of Serotonin Synthesis by P-Chlorphenylanine Prevents the Forgetting of Contextual Memory After Reminder and the Protein Sythesis Inhibition", Frontiers in Phamacology. 9(607). pp. 1-10. (Year: 2018).*
Sheehan, K. et al. "Tryptophan hydroxylase 2 (TPH2) gene variants associated with ADHD", Molecular Psychiatry. 10. pp. 944-949. (Year: 2005).*
Reynolds, G.P. et al. "Brain Neurotransmitter Deficits in Mice Transgenic for the Huntington's Disease Mutation", Journal of Neurochemistry. 72(4). pp. 1773-1776. (Year: 1999).*
Pla, P. et al. "Mood disorders in Huntington's disease: from behavior to cellular and molecular mechanisms", Frontiers in Behavioral Neuroscience. 8(135). pp. 1-15. (Year: 2014).*
Dupuis, L. et al. "Platelet Serotonin Level Predicts Survival in Amyotrophic Lateral Sclerosis", PloSone. 5(10). pp. 1-5. (Year: 2010).*
Sarva, H. et al. "Treatment Options in Degenerative Cerebellar Ataxia: A Systematic Review", Movement Disorders. 1(4). pp. 291-298. (Year: 2014).*
Rohr, A et al. "Citalopram, a selective serotonin reuptake inhibitor, improves symptoms of Friedreich's ataxia", Pharmacopsychiatry. 32(3). Abstract. (Year: 1999).*
Monte, T.L. et al. "Use of fluoxetine for treatment of Machado-Joseph disease: an open-label study", Acta Neurologica Scandinavica. 107(3). Abstract. (Year: 2003).*
Smith, G.S. et al. "Molecular Imaging of Serotonin Degeneration in Mild Cognitive Impairment", Neurobiology of Disease. 105. pp. 1-28. (Year: 2017).*
Smit, M. et al. "Serotonergic perturbations in dystonia disorders—a systematic review", Neuroscience and Biobehavioral Reviews. 65. pp. 264-275. (Year: 2016)*
Kin's lactic acid bacteria and fermented, vol. 8, 2011, & its English translation only the parts from this document cited in this OA.
JPO, Office Action of JP 2020-541769 dated Jul. 27, 2021.
Andrea Ruth McDowell, "Optimally lyophilized Lactobacillus plantarum SNUG 12071 survival under storage and gastrointestinal conditions", Masters Thesis, Seoul National University.
Yen-Wenn Liu et al., "Psychotropic effects of Lactobacillus plantarum PS128 in early life-stressed and naive adult mice", 2016, Brain Research, vol. 1631, pp. 1-12.
Apo, Office Action of AU 2019216129 dated Aug. 23, 2021.
Davis D. J. et al., "Lactobacillus plantarum attenuates anxiety-related behavior and protects against stress-induced dysbiosis in adult zebrafish", Sci. Rep. Sep. 19, 2016, vol. 6, p. 1-11.
Kipo, PCT Search Report & Written Opinion of PCT/KR2019/001525 dated Apr. 29, 2019.
Daniel J. Davis et al., "Lactobacillus plantarum attenuates anxiety-related behavior and protects against stress-induced dysbiosis in adult zebrafish", Scientific Reports, Sep. 19, 2016, 6, 1-11. DOI: 10.1038/srep33726.
Caroline J. K. Wallace et al., "The effects of probiotics on depressive symptoms in humans: a systematic review", Ann. Gen. Psychiatry, Feb. 20, 2017, 16, 1-10. DOI 10.1186/S12991-017-0138-2.
Monsheel S. K. Sodhi et al., "Serotonin and Brain Development", Int Rev Neurobiol 2004, 59, 111-174.
Robert E. Becker et al., "Mechanisms of Cholinesterase Inhibition in Senile Dementia of the Alzheimer Type: Clinical, Pharmacological, and Therapeutic Aspects", Drug Development Research, 1988, 12, 163-195.
Report of a joint FAO/WHO working group on drafting guidelines for the evaluation of probiotics in food, London Ontario, Canada, Apr. 30 and May 1, 2002.
L. Lachman et al., "Tablet Coating", The Theory and Practice of Industrial Pharmacy, 3, 1986, pp. 365~373.
Anonymous, "Therapeutic Incompatibility", Remington's Pharmaceutical Sciences, 13, pp. 1689~1691 (Mack Publ., Co., 1970).
Slyter, L. L, "Influence of Acidosis on Rumen Function ", J. Animal Sci.1976, 43. 910-926.
Johnson, D. E et al., "Nutrient Digestibility of Brewers Single Cell Protein", J. Anim. Sci.,1983, 56, 735-739.
Williams, P. E. V. et al., "Rumen Probiosis: the Effects of Novel Microorganisms on Rumen Fermentation and Ruminant Productivity", Butterworths, 1990, 211-227.
Kyeongju Lee, "Inhibitory effect of Lactobacillus spp. isolated from healthy Korean women on vaginal pathogens", Seoul University, 2017.
Soobin Yoon, "In Vitro Inhibitory Effect by Korean Intestinal Microbial Isolates on Clostridium difficile", Seoul University, 2016.
Yongbin Choi, "Social defeat stress induced dysbiosis of gut microbiota and its attenuation via Lactobacillus plantarum treatment", Seoul University, 2017.
Meina Lin, "Screening and evaluation of Lactobacillus spp. tightening the intestinal barrier", Seoul University, 2017.
EPO, search report of the corresponding EP Patent Application No. 19747730.0, dated Oct. 1, 2021.

* cited by examiner

LACTOBACILLUS PLANTARUM KBL396 STRAIN AND USE THEREOF

A Sequence Listing submitted as an ASCII text file via EFS-Web is hereby incorporated by reference in accordance with 35 U.S.C. § 1.52 (e). The name of the ASCII text file for the Sequence Listing is LPP20202479US_sequence_listing.txt, the date of creation of the ASCII text file is Jul. 13, 2020, and the size of the ASCII text file is 3,613 bytes.

FIELD OF THE INVENTION

The present invention relates to a novel *Lactobacillus plantarum* KBL396 strain and use thereof, and more specifically, relates to a novel probiotic, *Lactobacillus plantarum* KBL396 strain, a composition containing its live cell, killed cell, culture, lysate or extract, and food and medicinal use for improving human mental health thereof.

BACKGROUND ART

Probiotics refer to microorganisms having the antimicrobial activity and enzymatic activity to help balance of intestinal microorganisms and products produced by the microorganisms. In addition, probiotics are defined as live cells in the form of single or complex strains that are supplied to humans or animals in the form of dry cells or fermentation products to improve intestinal microflora. The characteristics that probiotics must possess are having the intestine of humans as a habitat, having non-pathogenic and non-toxic properties and surviving while going to the intestine. Furthermore, it must maintain the viability and activity before being consumed in the food being delivered, be sensitive to antibiotics used to prevent infection, and not have an antibiotic-resistant plasmid. Moreover, it must have resistance to acids, enzymes and bile in the intestinal environment.

These probiotics include *Bacillus* sp., which has excellent ability to produce digestive enzymes (amylase, protease, lipase, cellulase, phosphatase), *Lactobacillus* sp., which produces lactic acid, and photosynthetic bacteria, which prevents odors by using substances causing odors that remain in animal feces (ammonia, hydrogen sulfide, amines, etc.) in metabolic processes. Recently, as probiotics have been reported to improve various health functions, including improving intestinal health, it has been spotlighted as a major therapeutic agent that can replace therapeutic agents based on conventional compounds.

As neurological diseases, due to rapidly increasing stress in modern society, mental disorders including anxiety, depression, schizophrenia, cognitive disorders, and the like, and neurodegenerative diseases, which are characterized by gradual loss of neurons of the central nervous system (CNS) and/or peripheral nervous system (PNS) that is related to aging and is often accompanied by degeneration or loss of at least one of memory, motor ability, cognitive ability and sensory ability, along with other neurological deficits, have been increasing.

It has been reported that patients with mental disorders may lead to suicide accidents in severe cases, and in particular, more than half of depressed patients consider suicide, and actually, it is known that 10 to 15% of patients commit suicide. Depression is a disease that has decrease of will and depression as major symptoms, and causes various mental and physical symptoms and decreases daily functions, and it has been reported that about 15 to 20% of the prevalence of life is a depressive disorder. The cause of depression is not yet clear, but it is known that various biochemical, genetic and environmental factors cause disease as other mental diseases. The prevalence of life of depression is about 10 to 25% for women and 5 to 12% for men, and the frequency is twice as high in women.

Like this, depression occurs a representative high-frequency disease today, and depression is a disease that worsens the mind and body at the same time, and if left untreated, it may last for several months to several years, and lead to collapse of human relations or loss of professional productivity, and incapacity to lead to death, and therefore it may put a heavy burden on not only patients but also families and society.

Although the above severity of depression has been reported, the cause of depression and the action mechanism of antidepressants have not been fully understood yet. However, in general, it is widely known in the academic world that depression is caused by a lack of serotonin (5-HT), which is a monoamine-based neurotransmitter in the synapse of the central nervous system (Sodhi M S et al, Int Rev Neurobiol 2004, 59, 111-174).

Most antidepressants currently used in clinical practice are drugs that enhance the action of monoamine-based neurotransmitters, and substances that inhibit decomposition of serotonin or dopamine, or the like, such as substances inhibiting reabsorption of serotonin or norepinephrine in neurons (SSRI, SNRI, TCAs, etc.), and monoamine oxidase inhibitors. However, currently, only about 10-25% of Korean depression patients are receiving antidepressant treatment, and about 40% of them are known to stop treatment as the compliance is reduced due to side effects, etc., and furthermore, it has been reported that non-responders who do not respond even when taking antidepressants account for 33%, and therefore there is a need to develop a new more effective therapeutic agent.

In addition, neurodegenerative diseases are symptoms in which brain function is impaired by various causes, and cognitive function is continuously and overall deteriorated compared to the previous one, resulting in significant disruption in daily life, and this cognitive impairment has a clinical feature of progressive loss of memory, cognition, reasoning, judgement and emotional stability, which gradually leads to mental devastation and eventually causes death.

As an example of such a disease, Alzheimer's disease (AD) is a common cause of progressive mental dysfunction (dementia) in the elderly and is considered the fourth leading cause of medical death in the United States. In particular, Alzheimer's disease is associated with degeneration of cholinergic neurons at the base of the forebrain, which plays a fundamental role in cognitive action, including memory (Becker et al., Drug Development Research, 1988, 12, 163-195). In addition, cognitive disorders and degenerative brain disorders have been found worldwide in various races and tribes and have become a major public health problem. Currently, these diseases are estimated to affect about 2 million to 3 million people in the United States alone, but treatment with currently used drugs is impossible to treat and it is increasing worldwide as human lifespan increases, and therefore it is important to pay attention to prevent it at the early stage.

Against this background, there is an urgent need to develop an effective therapeutic agent for neurological diseases.

SUMMARY OF THE INVENTION

To solve the above problems, the present inventors have identified a strain showing an excellent effect on improvement of neurological diseases by screening various probiotic strains, considering that the health enhancement effect of probiotics is not a general characteristic of genus and species and is specific to a certain strain (Report of a joint FAO/WHO working group on drafting guidelines for the evaluation of probiotics in food, London Ontario, Canada, 2002), and have completed the present invention.

Accordingly, an object of the present invention is to provide a novel lactic acid bacterium.

In addition, another object of the present invention is to provide various food and medicinal uses of the novel lactic acid bacterium.

To achieve the above objects, the present invention provides a *Lactobacillus plantarum* KBL396 (KCTC13278BP).

The present invention also provides a pharmaceutical composition comprising at least one selected from the group consisting of the strain, culture of the strain, lysate of the strain and extract of the strain.

The present invention also provides a pharmaceutical composition for preventing or treating neurological diseases comprising at least one selected from the group consisting of the strain, culture of the strain, lysate of the strain and extract of the strain.

The present invention also provides a food composition for preventing or improving neurological diseases comprising at least one selected from the group consisting of a *Lactobacillus plantarum* KBL396 (KCTC13278BP), culture of the strain, lysate of the strain and extract of the strain.

The present invention also provides an additive for animal feed comprising at least one selected from the group consisting of a *Lactobacillus plantarum* KBL396 (KCTC13278BP), culture of the strain, lysate of the strain and extract of the strain.

The present invention also provides a method for prevention or treatment of neurological diseases comprising administering at least one selected from the group consisting of a *Lactobacillus plantarum* KBL396 (KCTC13278BP), culture of the strain, lysate of the strain and extract of the strain, to a subject in need thereof a therapeutically effective amount.

The present invention also provides a composition comprising at least one selected from the group consisting of a *Lactobacillus plantarum* KBL396 (KCTC13278BP), culture of the strain, lysate of the strain and extract of the strain for use in prevention or treatment of neurological diseases.

The present invention also provides a use of a composition comprising at least one selected from the group consisting of the strain, culture of the strain, lysate of the strain and extract of the strain, for the manufacture of a drug for prevention or treatment of neurological diseases.

The present invention also provides a food composition for preventing or improving neurological diseases comprising at least one selected from the group consisting of the strain, culture of the strain, lysate of the strain and extract of the strain.

DETAILED DESCRIPTION OF THE INVENTION AND PREFERRED EMBODIMENTS

Figure 1A:
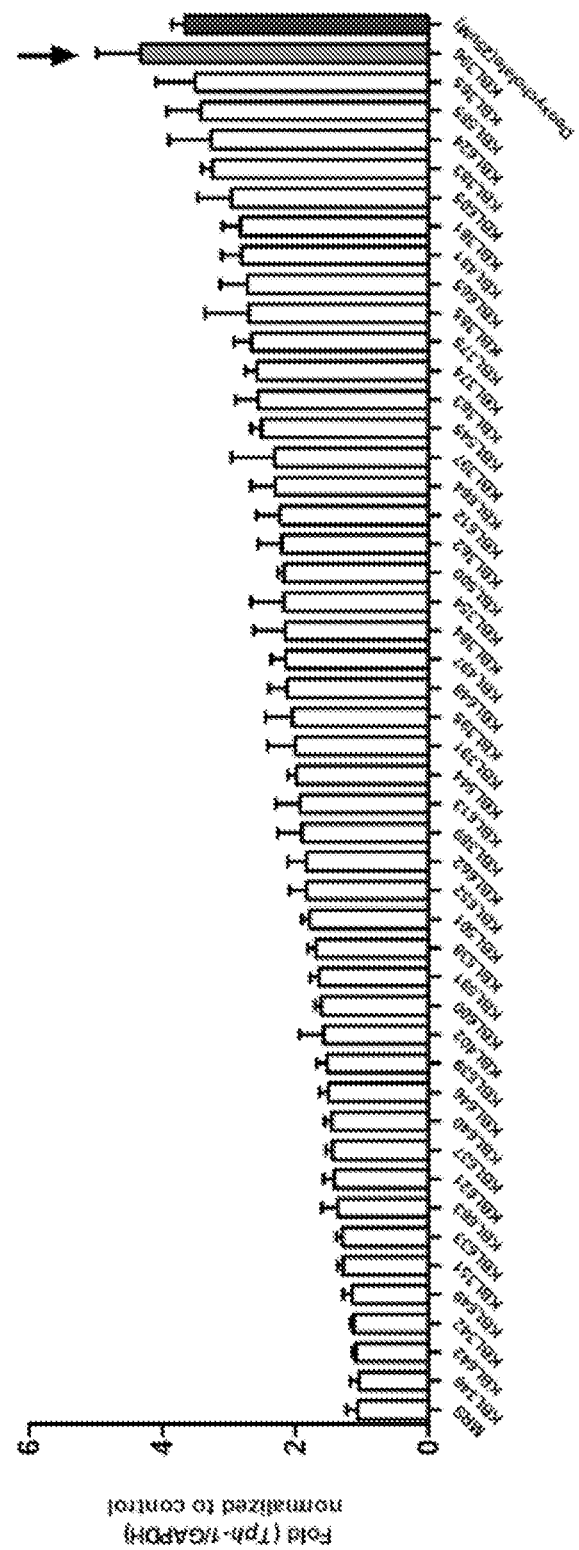
FIG. 1 is the result of comparing the effect on expression of TPH-1 that is a rate-limiting enzyme of a serotonin biosynthetic pathway of various *Lactobacillus* and *Bifidobacterium* strains (A) and the result of confirming the difference of the effect on expression of TPH-1 of *Lactobacillus plantarum* KBL396 strain compared to commercially available strains (B).

Unless defined otherwise, all technical and scientific terms used herein have the same meaning as commonly understood by those skilled in the art to which the present invention pertains. In general, the nomenclature used herein is well known and commonly used in the art.

In the present invention, the serotonin biosynthesis abilities of various probiotic strains derived from humans were compared, and it was confirmed that *Lactobacillus plantarum* KBL396 strain among them particularly showed an excellent effect on the serotonin biosythesis, and its excellent effect of prevention, improvement and treatment for neurological diseases. In addition, as the result of analyzing 16s rDNA of the strain, the strain is confirmed as a novel strain which has not been known in the prior art.

According to an embodiment of the present invention, the present invention provides a *Lactobacillus plantarum* KBL396 (KCTC13278BP).

The strain according to the present invention is characterized in that it includes 16s rDNA sequence represented by SEQ ID NO: 1.

<SEQ ID NO: 1>
TATCAGTACGTGCTATAATGCAGTCGACGACTCTGGTATTGATTGGTGC

TTGCATCATGATTTACATTTGAGTGAGTGGCGAACTGGTGAGTAACACG

TGGGAAACCTGCCCAGAAGCGGGGGATAACACCTGGAAACAGATGCTAA

```
-continued
TACCGCATAACAACTTGGACCGCATGGTCCGAGCTTGAAAGATGGCTTC

GGCTATCACTTTTGGATGGTCCCGCGGCGTATTAGCTAGATGGTGGGGT

AACGGCTCACCATGGCAATGATACGTAGCCGACCTGAGAGGGTAATCGG

CCACATTGGGACTGAGACACGGCCCAAACTCCTACGGGAGGCAGCAGTA

GGGAATCTTCCACAATGGACGAAAGTCTGATGGAGCAACGCCGCGTGAG

TGAAGAAGGGTTTCGGCTCGTAAAACTCTGTTGTTAAAGAAGAACATAT

CTGAGAGTAACTGTTCAGGTATTGACGGTATTTAACCAGAAAGCCACGG

CTAACTACGTGCCAGCAGCCGCGGTAATACGTAGGTGGCAAGCGTTGTC

CGGATTTATTGGGCGTAAAGCGAGCGCAGGCGGTTTTTTAAGTCTGATG

TGAAAGCCTTCGGCTCAACCGAAGAAGTGCATCGGAAACTGGGAAACTT

GAGTGCAGAAGAGGACAGTGGAACTCCATGTGTAGCGGTGAAATGCGTA

GATATATGGAAGAACACCAGTGGCGAAGGCGGCTGTCTGGTCTGTAACT

GACGCTGAGGCTCGAAAGTATGGGTAGCAAACAGGATTAGATACCCTGG

TAGTCCATACCGTAAACGATGAATGCTAAGTGTTGGAGGGTTTCCGCCC

TTCAGTGCTGCAGCTAACGCATTAAGCATTCCGCCTGGGGAGTACGGC

CCGCAAGGCTGAAACTCAAAGGAATTGACGGGGGCCCGCACAAGCGGT

GGGAGCATGTGGGTTTAATTCAAAGCTACGCGAAGAAACCTTACCCAGG

TTTTGACATACTAATGCAAATTCTAAAGAGATTAGAACGTTTCCCTTCC

GGGGACATGGGATACCGGTGGGTGCATGGGTTGGTCGTCAGCTTCGTG

GTCGTGAGAATGTTTGGGTTTAAGTTCCCCGAAACGAGCGCAACCCTTA

TTATCAGTTGCCAGCATTAAGTTGGGCACTCTGGTGAGACTGCCGGTGA

CAAACCGGAGGAAGGTGGGGATGACGTCAAATCATCATGCCCCTTATGA

CCTGGGCTACACACGTGCTACAATGGATGGTACAACGAGTTGCGAACTC

GCGAGAGTAAGCTAATCTCTTAAAGCCATTCTCAGTTCGGATTGTAGGC

TGCAACTCGCCTACATGAAGTCGGAATCGCTAGTAATCGCGGATCAGCA

TGCCGCGGTGAATACGTTCCCGGGCCTTGTACACACCGCCCGTCACACC

ATGAGAGTTTGTAACACCCAAAGTCGGTGGGGTAACCTTTAGAACCAGC

CGCCTAATGGCACCACCATGCG
```

The strain according to the present invention is characterized by exhibiting at least one of properties selected from the group consisting of serotonin secretion increase, inflammatory cytokine expression inhibition, reduction of intestinal harmful bacteria and anti-oxidant action.

In addition, the strain according to the present invention may use as a carbon source at least one selected from the group consisting of D-ribose, D-galactose, D-glucose, D-fructose, D-mannose, mannitol, sorbitol, α-methyl-D-mannoside, α-methyl-D-glucoside, N-acetyl-glucosamine, amygdalin, arbutin, esculin, salicin, cellobiose, maltose, lactose, melibiose, sucrose, trehalose, melezitoze and gentiobiose.

In addition, the strain according to the present invention has an activity of at least an enzyme selected from the group consisting of leucine arylamidase, valine arylamidase, α-glucosidase and β-glucosidase.

The *Lactobacillus plantarum* KBL396 (KCTC13278BP) according to the present invention exhibit an excellent effect on improvement of neurological diseases without risk of side effects of conventional therapeutic agents used for neurological diseases, in addition to advantages of being safe and non-toxic in a human body, and being easily accessible without negative recognition as a therapeutic agent, and therefore it may be very usefully used industrially.

According to another embodiment of the present invention, the present invention provides a pharmaceutical composition comprising at least one selected from the group consisting of the *Lactobacillus plantarum* KBL396 (KCTC13278BP), culture of the strain, lysate of the strain and extract of the strain.

Herein, the term, "culture" means a product obtained by culturing a lactic acid bacterium in a known medium, and the product may include a lactic acid bacterium. The medium may be selected from a known liquid medium or solid medium, and for example, it may be MRS liquid medium, GAM liquid medium, MRS agar medium, GAM agar medium, or BL agar medium, but not limited thereto. Herein, the term, "lysate" means a lactic acid bacterium destroyed by enzyme treatment, homogenization or ultrasonication of the lactic acid bacterium. Moreover, herein, the term, "extract" means a product obtained by extracting a lactic acid bacterium with a known extraction solvent. Furthermore, herein, the term, "live cell" means the novel lactic acid bacterium of the present invention itself, and "killed cell" means a lactic acid bacterium sterilized by heating, pressurization or drug treatment, or the like.

The pharmaceutical composition according to the present invention has an excellent effect on prevention or treatment of neurological diseases, and exhibits an excellent effect as a pharmaceutical composition through recovery of intestinal microflora, anti-oxidant effect, immunoregulatory effect, and the like.

The pharmaceutical composition of the present invention may further comprise at least one pharmaceutically acceptable excipient and/or freeze-drying agent.

The term, "pharmaceutically acceptable" refers to one which is physiologically acceptable and usually does not cause severe gastrointestinal disorders, dizziness, allergic reactions or similar reactions when administered to humans.

The composition according to the present invention may further comprise at least one pharmaceutically acceptable excipient in addition to the novel lactic acid bacterium. The excipient to be comprised in the composition of the present invention may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, and the like, but not limited thereto.

The composition of the present invention may be formulated in formulations for oral administration or formulation for parenteral administration by a common method, and when formulated, it may be produced using a commonly used filler, thickener, binder, wetting agent, disintegrating agent, surfactant, cryoprotectant, and the like.

When the composition of the present invention is formulated as a solid preparation for oral administration, tablets, pills, powders, granules, capsules and the like are included, and such a solid preparation may comprise at least one excipient, for example, starch, calcium carbonate, sucrose, lactose or gelatin, or the like, in addition to active ingredients. In addition, it may comprise a lubricant such as magnesium stearate and talc, and the like, in addition to simple excipients, but not limited thereto.

When the composition of the present invention is formulated as a liquid preparation for oral administration, suspension, oral liquids, emulsifiers and syrup, and the like are included, and various excipients, for example, wetting agents, sweeteners, flavors, preservatives, and the like may be included in addition to commonly used simple diluents, such as water and liquid paraffin, but not limited thereto.

When the composition of the present invention is formulated as a preparation for parenteral administration, sterile aqueous solution, non-aqueous solvent, suspension, emulsifiers and suppositories may be included. As the non-aqueous solvent and suspension, propylene glycol, polyethylene glycol, plant oils such as olive oil, injectable ester such as ethyl oleate, and the like may be included, but not limited thereto. As a base compound of suppositories, witepsol, macrogol, tween 61, cacao butter, laurinum, glycerogelatin, and the like may be used.

The content of the novel lactic acid bacterium, and the like which are active ingredients of the pharmaceutical composition of the present invention may be adjusted in various ranges according to the specific form, purpose of use and aspects of the composition. In the pharmaceutical composition according to the present invention, the content of the active ingredients is not greatly limited, and for example, it may be 0.01 to 99% by weight, specifically, 0.1 to 75% by weight, more specifically, 0.5 to 50% by weight, based on the total weight of the composition.

The cryoprotectant used in the present invention is used to preserve the probiotic formulation during freeze-drying and improve a shelf-life. The cryoprotectant used in the present invention may comprise a general saccharide. The saccharide may be a mono-, di-, oligo-, or poly-saccharide or a mixture of at least 2 or more of saccharides.

For example, a cryoprotectant selected from the group consisting of sucrose, maltose, maltodextrin, trehalose, mannitol, sorbitol, inulin, glycerol, DMSO, ethylene glycol, propylene glycol, 2-methyl-2,4-pentanediol, polyethylene glycol, polyvinyl pyrrolidone, polyvinyl alcohol, polyglycerol, skimmed milk, milk protein, whey protein, betaine, adonitol, lactose or any combination thereof may be used.

Preferably, the cryoprotectant, may include at least one selected from the group consisting of sucrose, skimmed milk and sorbitol. More preferably, sucrose, skimmed milk and sorbitol may be contained, and specifically, 2 to 20% by weight of sucrose, 2 to 20% by weight of sorbitol and 5 to 30% by weight of skimmed milk based on the total weight of the composition may be included. By the addition of the cryoprotectant, the freeze-dried lactic acid bacterium may show significantly increased viability, storage stability, acid resistance and bile resistance.

In addition, the addition of anti-oxidants such as riboflavin, riboflavin phosphate or its physiological acceptable salt, glutathione, ascorbate, glutathione and cysteine to the freeze-dried composition according to the present invention may further increase the viability of the strain during the storage.

According to other embodiment of the present invention, the present invention provides a pharmaceutical composition for prevention or treatment of neurological diseases comprising at least one selected from the group consisting of the *Lactobacillus plantarum* KBL396 (KCTC13278BP), culture of the strain, lysate of the strain and extract of the strain.

Herein, the term, "prevention" means all actions of inhibiting symptoms of neurological diseases or delaying progression by administration of the pharmaceutical composition of the present invention.

Herein, the term, "treatment" means all actions of improving or beneficially altering symptoms of neurological diseases by administration of the pharmaceutical composition of the present invention.

Herein, "neurological disease" includes all pathological conditions derived from pathology of the nervous system. Accordingly, the present invention is objected to prevent or treat acute and/or chronic diseases related to nerves, neuropsychiatry, psychiatry, neuropathy and neurodegeneration.

This neurological disease may be a mental disorder or neurodegenerative disease.

Non-limitative examples of the mental disorder may include stress-induced tension, anxiety, depression, mood disorder, insomnia, delusional disorder, obsessive compulsive disorder, migraine, memory disorder, cognitive disorder, attention disorder, and the like. In addition, non-limitative examples of the neurodegenerative disease may include Parkinson's disease, Huntington's disease, Alzheimer's disease, amyotrophic lateral sclerosis, spinocerebellar Atrophy, Tourette's Syndrome, Friedrich's Ataxia, Machado-Joseph's disease, dementia, dystonia, progressive supranuclear palsy, and the like.

The pharmaceutical composition for preventing or treating neurological diseases according to the present invention exhibits an excellent effect on improvement of neurological diseases without risk of side effects of conventional therapeutic agents of neurological diseases, in addition to advantages of being non-toxic in a human body and safe, and easily accessible without negative recognition as a therapeutic agent, and therefore it may be very usefully used industrially. According to one embodiment according to the present invention, the composition of the present invention has an effect of prevention, improvement and treatment for neurological diseases by inducing serotonin biosynthesis. According to another embodiment of the present invention, the composition of the present invention exhibits an excellent effect on cognitive ability improvement. According to other embodiment of the present invention, the composition of the present invention exhibits an excellent effect on improvement of symptoms such as tension, depression, anxiety, and the like, under the stress environment. According to other embodiment of the present invention, the composition of the present invention exhibits an excellent effect on prevention, treatment and improvement of neurological diseases by regulating the inflammatory reaction of the nerve system. According to other embodiment of the present invention, the composition of the present invention exhibits an excellent effect on prevention, improvement and treatment for neurological diseases by regulating the inflammatory reaction. According to other embodiment of the present invention, the composition of the present invention exhibits an excellent effect on prevention, improvement and treatment for neurological disease by regulating the inflammatory reaction in nerves and brain due to immune imbalance.

The dose of the pharmaceutical composition according to the present invention should be a pharmaceutically effective amount. "Pharmaceutically effective amount" means a sufficient amount for preventing or treating neurological diseases at a reasonable benefit/risk ratio applicable to medical treatment. The effective dose level may be variously selected by those skilled in the art according to factors such as formulation method, patient's condition and body weight, patient's gender, age, degree of disease, drug form, administration route and period, excretion rate, reaction sensitivity, and the like. The effective dose may be altered according to the route of treatment, use of excipients and possibility capable of being used with other drugs, as recognized to those skilled in the art. However, for a preferable effect, in case of oral administration preparations, generally, the composition of the present invention may be administered in an amount of 0.001 to 1000 mg/kg, preferably, 0.01 to 100 mg/kg a day, to an adult.

When administering the administration preparation as above, the *Lactobacillus plantarum* KBL396 (KCTC13278BP) of the present invention may be administered by $1 \times 10^3$ CFU/kg to $1 \times 10^{11}$ CFU/kg a day. The administration may be performed once a day or several times divided. The dose is not intended to limit the scope of the present invention in any aspect.

The pharmaceutical composition according to the present invention may be administered through various routes to a mammal including a mouse, livestock, human and the like. Specifically, the pharmaceutical composition of the present invention may be orally or parenterally administered (for example, applied or injected intravenously, subcutaneously, intraperitoneally), but oral administration is preferable. Solid preparations for oral administration may include powders, granules, tablets, capsules, soft capsules, pills, and the like.

The pharmaceutical composition of the present invention may be provided as an enteric coated enteric preparation, particularly, as an oral unit formulation. Herein, "enteric coating" includes all kinds of pharmaceutically acceptable coatings known, which are not decomposed by gastric acid and therefore, are maintained, but are sufficiently decomposed in the small intestine and make active components to be released into the small intestine. The "enteric coating" of the present invention refers to coatings which are maintained for 2 hours or more as they are, when contacting the artificial gastric juice such as HCl solution of pH 1 at 36° C. to 38° C. and preferably, after that, are decomposed in the artificial intestinal juice such as $KH_2PO_4$ buffer solution of pH 6.8 within 30 minutes.

The enteric coating of the present invention is coated in an amount of about 16 to 30, preferably, 16 to 20 or 25 mg, per 1 core. When the thickness of the enteric coating of the present invention is 5 to 100 μm, preferably, 20 to 80 μm, a satisfactory result is shown. The materials of the enteric coating are appropriately selected from known polymer substances. The appropriate polymer substances are listed in many documents (L. Lachman et al., The Theory and Practice of Industrial Pharmacy, 3 edition, 1986, pp. 365-373; H. Sucker et al., Pharmazeutische Technologie, Thieme, 1991, pp. 355-359; Hagers Handbuchder pharmazeutischen Praxis, 4 edition, Vol. 7, pp. 739-742, and 766-778, (SpringerVerlag, 1971); and Remington's Pharmaceutical Sciences, 13 edition, pp. 1689-1691 (Mack Publ., Co., 1970)), and cellulose ester derivatives, cellulose ether, methylacrylate copolymer of acrylic resin and copolymer of maleic acid and phthalic acid derivatives may be comprised thereto.

The enteric coating of the present invention may be prepared using a common enteric coating method which sprays an enteric coating solution to a core. As an appropriate solvent used for the enteric coating process, alcohols such as ethanol, ketones such as acetone, halogenated hydrocarbon solvents such as dichloromethane ($CH_2Cl_2$) and mixed solvents of these solvents may be used. A softener such as di-n-butylphthalate or triacetin is added to the coating solution at a ratio of 1 to about 0.05 to about 0.3 (coating material to softener). It is suitable to perfume the spraying process continuously, and it is possible to regulate the spraying amount considering the condition of coating.

The spraying pressure may be variously adjusted, and in general, a satisfiable result is obtained by the spraying pressure of about 1 to about 1.5 bar.

Oral liquid preparations are suspension, oral liquids, emulsifiers, syrup, aerosol, and the like, and may include various excipients, for example, wetting agents, sweeteners, flavors, preservatives, and the like, in addition to commonly used simple diluents, water and liquid paraffin. As preparations for parenteral administration, it may be used by being formulated in a form of external liquid and sterile injection such as sterile aqueous solution, liquids, non-aqueous solvent, suspension, emulsion, eye drops, eye ointment, syrup, suppositories, aerosol, and the like, which are sterilized according to commonly used method. Preparations for local administration may be anhydrous or aqueous, depending on the clinical prescription. As the non-aqueous solvent and suspension, propylene glycol, polyethylene glycol, plant oils such as olive oil, injectable ester such as ethyl oleate, and the like may be used.

The pharmaceutical composition for prevention or treatment of neurological diseases according to the present invention may further contain at least one of known active ingredients having an effect of prevention or treatment of neurological diseases.

According to other embodiment of the present invention, the present invention provides a food composition for preventing or improving neurological diseases comprising at least one selected from the group consisting of the *Lactobacillus plantarum* KBL396 (KCTC13278BP), culture of the strain, lysate of the strain and extract of the strain.

The food composition according to the present invention is characterized by a composition for food or food additives, but not limited thereto, and it may be easily utilized as food having an effect on prevention or improvement of neurological diseases, for example, main ingredients of food, supplementary ingredients, food additives, health functional food or functional beverages.

The food means natural products or processed products containing one kind or more of nutrients, and preferably, means that it is ready to be eaten directly after some processing, and as a common meaning, includes all of food, food additives, health functional food and functional beverages.

The food to be added in the food composition according to the present invention includes for example, various kinds of food, beverages, gum, tea, vitamin complexes, functional food, and the like. Further, the food of the present invention include special nutrient food (e.g., formulas, infant and baby food, etc.), processed meat products, fish products, tofu, jellied food, noodles (e.g., ramen, noodles, etc.), breads, health supplement foods, seasonings (e.g. soy sauce, soybean paste, red pepper paste, mixed sauce, etc.), sauces, confectionary (e.g., snacks), candies, chocolate, gum, ice cream, dairy products (e.g., fermented milk, cheese, etc.), other processed food, Kimchi, pickled food (various kinds of Kimchi, pickled vegetables, etc.), beverages (e.g., fruit beverages, vegetable beverages, soybean milk products, fermented beverages, etc.) and natural seasoning (e.g., ramen soup, etc.), but not limited thereto. The food, beverage or food additive may be prepared by a common preparation method.

The health functional food means a food group in which added values are provided to act and express the function of the corresponding food for a specific purpose using a physical, biochemical or biotechnological method, or the like, or a food designed and processed to sufficiently express the body control function related to the biological defense rhythm control, disease prevention and recovery, and the like of the food composition. The functional food may comprise a food acceptable food supplement additive, and may further comprise an appropriate carrier, excipient and diluent commonly used in the manufacture of the functional food.

Herein, the functional beverage refers to the general term of drinking to relieve thirst or enjoy the taste, and there is no particular limitation on other components in addition to including the composition for improvement or prevention of symptoms of neurological diseases at the indicated ratio as essential components, and it may contain various flavoring agents or natural carbohydrates, and the like, as additional components, as common beverages.

Furthermore, in addition to the aforementioned ones, the food containing the food composition for improvement or prevention of symptoms of neurological disease of the present invention may contain various nutrients, vitamins, minerals (electrolytes), flavors such as synthetic flavors and natural flavors, coloring agents and fillers (cheese, chocolate, etc.), pectic acid and its salt, alginate and its salt, organic acids, protective colloidal thickeners, pH adjusting agents, stabilizers, preservatives, glycerin, alcohols, carbonating agents used for carbonated beverages, and the like, and the components may be used alone or in combination.

In the food containing the food composition of the present invention, the amount of the composition according to the present invention may be 0.001% by weight to 100% by weight, preferably, 1% by weight to 99% by weight, of the total food weight, and in case of beverages, it may be comprised at a ratio of 0.001 g to 10 g, preferably, 0.01 g to 1 g, based on 100 ml, but it may be less than the range, for long-term intake for health and hygiene purposes or health control, and since the active ingredients have no problem in the aspect of safety, it may be used in an amount over the range, and therefore it is not limited to the range.

The food composition of the present invention may further comprise at least one of excipients and/or freeze-drying agents.

The food composition of the present invention may be prepared in a form of a composition suitable to add the *Lactobacillus plantarum* KBL396 strain independently or to an acceptable carrier, or to be ingested by humans or animals. In other words, it may be used by being added to food which does not contain other probiotic bacteria and food already containing various kinds of probiotic bacteria. For example, in preparation of the food of the present invention, other microorganisms usable together with the strain of the present invention are not particularly limited, as long as they are appropriate to be ingested by humans or animals and have the probiotic activity which can inhibit pathogenic harmful bacteria or improve the balance of microorganisms in the mammalian intestine when ingested. As examples of these probiotic microorganisms, there are yeasts including *Saccharomyces, Candida, Pichia* and *Torulopsis*, mold such as *Aspergillus, Rhizopus, Mucor, Penicillium*, and the like, bacteria belonging to *Lactobacillus, Bifidobacterium, Leuconostoc, Lactococcus, Bacillus, Streptococcus, Propionibacterium, Enterococcus, Pediococcus* genera, and the like. Specific examples of the appropriate probiotic microorganisms include *Saccharomyces cerevisiae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus delbruckii, Lactobacillus johnsonii, Lactobacillus farciminus, Lactobacillus gasseri, Lactobacillus helveticus, Lactobacillus rhamnosus, Lactobacillus reuteri, Lactobacillus sakei, Lactococcus lactis, Pediococcus acidilactici*, and the like. Preferably, the effect may be further enhanced by additionally comprising probiotic microorganism mixed bacteria having excellent probiotic activity and simultaneously having an excellent effect of improvement of neurological diseases in the composition for food of the present invention. Examples of the carrier to be used in the composition for food of the present invention may include extenders, high fiber additives, encapsulating agents, lipids and the like, and the examples of the carrier are sufficiently known in the art. The *Lactobacillus plantarum* KBL396 of the present invention may be in a freeze-dried or capsulated form or a form of culture suspension or dried powder.

According to other embodiment of the present invention, the present invention provides an additive for animal feed comprising at least one selected from the *Lactobacillus plantarum* KBL396 (KCTC13278BP), culture of the strain, lysate of the strain and extract of the strain.

The additive for animal feed of the present invention may further comprise at least one of excipients and/or freeze-drying agents.

The additive for animal feed of the present invention may be in a dried or liquid preparation from, and may further comprise other non-pathogenic microorganisms in addition to the *Lactobacillus plantarum* KBL396 strain. As the microorganisms to be added, for example, hay *bacillus* such as *Bacillus subtilis* capable of producing protease, lipase and carbonate converting enzyme, *Lactobacillus* strains having the physiological activity and decomposition ability of organic substances under an anaerobic condition such as stomach of cows, filamentous fungi such as *Aspergillus oryzae* showing effects of increasing the body weight of livestock and increasing the milk yield and raising the digestibility of feed (Slyter, L. L. J. Animal Sci. 1976, 43. 910-926) and yeasts such as *Saccharomyces cerevisiae* (Johnson, D. E et al. J. Anim Sci., 1983, 56, 735-739; Williams, P. E. V. et al, 1990, 211), and the like may be used.

The additive for animal feed of the present invention may further comprise at least one enzyme preparation in addition to the *Lactobacillus plantarum* KBL396. The enzyme preparation to be added is possibly in a dried or liquid condition, and as the enzyme preparation, lipolytic enzyme such as lipase, phytase producing phosphate and inositol phosphate by decomposition phytic acid, amylase which is enzyme hydrolyzing α-1,4-glycoside bond comprised in starch and glycogen, and the like, phosphatase that is enzyme hydrolyzing organic phosphate ester, carboxymethylcellulase decomposing cellulose, xylase decomposing xylose, maltase hydrolyzing maltose into glucose of two molecules and glycogenic enzyme such as invertase producing a glucose-fructose mixture by hydrolyzing saccharose, and the like may be used.

When the *Lactobacillus plantarum* KBL396 strain of the present invention is used as an additive for animal feed, as raw materials for feed, in addition to various kinds of grains and soybean proteins, peanut, pea, sugar beet, pulp, grain by-products, animal internal organ powder and fish meal powder, and the like may be used, and unprocessed or processed ones may be used without limitation. The processing process is not necessarily limited thereto, for example, a process of compressing to a certain outlet under pressure while feed raw materials are filled, and in case of protein, it is preferable to use extrusion, which denatures protein and increases the availability. The extrusion has advantages of denaturing protein and destroying anti-enzyme factors by a heat treatment process, and the like. In addition, in case of soybean protein, by extrusion, the digestibility of protein may be enhanced, and anti-nutritional factors such as a trypsin inhibitor that is one of inhibitors of protease present in soybean may be inactivated, and the enhancement of the digestibility by protease may be increased, and the nutritional value of soybean protein may be increased.

In other embodiment of the present invention, the present invention provides a method for prevention or treatment of neurological diseases comprising administering a therapeutically effective amount of at least one selected from the group consisting of the *Lactobacillus plantarum* KBL396 (KCTC13278BP), culture of the strain, lysate of the strain and extract of the strain to a subject in need thereof.

Herein, the term, "therapeutically effective amount (or, effective dose)" means an appropriate amount very sufficient to deliver a preferable effect, but adequate to prevent serious side effects within the scope of medical judgement. The amount of microorganisms to be administered into the body by the composition of the present invention may be suitably adjusted in consideration to the administration pathway and administration subject.

The "administration" means providing the prescribed pharmaceutical composition of the present invention by any appropriate method. Then, the subject means an animal, and typically, may be a mammal which can show a beneficial effect by treatment using the novel lactic acid bacterium of the present invention. As a preferable example of this subject, primates such as humans may be comprised. In addition, such subjects may include all subjects who have symptoms of or are at risk of having allergic diseases.

In other embodiment of the present invention, the present invention provides a composition comprising at least one selected from the group consisting of the *Lactobacillus plantarum* KBL396 (KCTC13278BP), culture of the strain, lysate of the strain and extract of the strain, to be used for prevention or treatment of neurological diseases.

Other embodiment of the present invention provides a use of a composition comprising at least one selected from the group consisting of the *Lactobacillus plantarum* KBL396 (KCTC13278BP), culture of the strain, lysate of the strain and extract of the strain, to prepare a drug for prevention or treatment of neurological diseases.

Hereinafter, the present invention will be described in more detail by examples. These examples are intended to illustrate the present invention only, and it is obvious to those skilled in the art that the scope of the present invention is not limited to these examples.

Example 1. Screening of Probiotic Strains Having Ability to Induce Serotonin Biosynthesis In many prior documents, it has been reported that serotonin plays an important role in neurological diseases, particularly, mental disorders. Using 47 kinds of probiotic strains isolated from infant and adult-derived feces (19 kinds *Lactobacillus* spp., 28 kinds *Bifidobacterium* spp.) and 2 strains of *Lactobacillus plantarum* sold as probiotics products, the ability to induce serotonin biosynthesis was evaluated. The ability to induce serotonin biosynthesis was confirmed by treating each strain to an enterochromaffin cell line, RIN14B, and observing how much the expression of the gene for TPH-1 (tryptophan hydroxylase-1), a rate-limiting enzyme of the serotonin biosynthesis pathway was promoted.

1-1. Culturing of Strains and Preparation of Culture Supernatant

To screen the novel strain showing an effective effect in neurological diseases, 47 kinds of candidate lactic acid bacteria isolated from feces of a healthy Korean male and female adult or infant were used. These candidate lactic acid bacteria were cultured in a 0.5% cysteine-added MRS medium, respectively, and were activated by subculturing twice at a 24-hour interval, and then the culture supernatant including metabolites of each strain was used in the experiment. After obtaining the culture supernatant, the pH of the supernatant obtained by centrifugation (13,000×g, 5 minutes, 4° C.) was calibrated to 7.0, and then sterilized using a filter in a 0.22 µm pore size, and stored at 4° C. before use.

The strains of lactic acid bacteria used for screening of novel strains were named KBL346, KBL642, KBL342, KBL649, KBL351, KBL633, KBL663, KBL621, KBL647, KBL640, KBL646, KBL639, KBL402, KBL600, KBL591, KBL538, KBL501, KBL652, KBL662, KBL389, KBL613, KBL544, KBL391, KBL395, KBL648, KBL497, KBL384, KBL354, KBL500, KBL362, KBL612, KBL664, KBL397, KBL545, KBL363, KBL374, KBL375, KBL385, KBL665, KBL481, KBL381, KBL605, KBL383, KBL624, KBL585, KBL365, or KBL39, respectively. Among the strains, 19 kinds of strains of KBL346, KBL342, KBL351, KBL402, KBL389, KBL391, KBL395, KBL384, KBL354, KBL362, KBL397, KBL363, KBL374, KBL375, KBL385, KBL381, KBL383, KBL365, and KBL396 were confirmed as *Lactobacillus* spp. strains, and 28 kinds of strains of KBL642, KBL649, KBL633, KBL663, KBL621, KBL647, KBL640, KBL646, KBL639, KBL600, KBL591, KBL538, KBL501, KBL652, KBL662, KBL613, KBL544, KBL648, KBL497, KBL500, KBL612, KBL664, KBL545, KBL665, KBL481, KBL605, KBL624 and KBL585 were confirmed as *Bifidobacterium* spp. strains.

In addition, as commercially available products, Solace (Oryx Biomedical Inc., Fremont, Calif., USA) consisting of *Lactobacillus plantarum* PS128 single strain product and *L. plantarum* (Quest Vitamins Limited, Kingstone, Hereford, UK) consisting of *Lactobacillus plantarum* 299v single strain product were purchased, respectively, and the culture supernatants of each strain was obtained through the culturing and activating processes of the same process as the candidate lactic acid bacteria to use it in the experiment.

1-2. Culturing of RIN14B Cell Line

The RIN14B (ATCC CRL-2059) cells were cultured under the condition of 37° C. and 5% $CO_2$ in RPMI 1640 medium in which 10% FBS, penicillin (100 µg/ml) and streptomycin (100 µg/ml) were added, and were subcultured once per 3 days. The RIN14B cell line was aliquoted by $4 \times 10^5$ cells/well in a 24 well plate, and then the bacterial culture supernatant was treated.

1-3. Treatment of Strain Culture Supernatant

After removing the medium from the RIN14B cell line aliquoted in the 24 well plate in Example 1-2, it was washed with PBS (500 µl/well) once. Then, the product was treated with 500 µl of the strain culture supernatant prepared in Example 1-1, or 500 µl of the diluted deoxycholate having ability to induce serotonin synthesis as a positive control group which was calibrated to 7.0 of pH and diluted in MRS medium sterilized with a filer to be the final concentration of 25 µM. After they were cultured for 1 hour under the condition of 37° C. and 5% $CO_2$, the cells and supernatant were collected to measure the expression of TPH1 (Tryptophan hydroxylase-1) enzyme.

1-4. Measurement of Tph1 Expression According to qRT-PCR Method

To measure the expression level of Tph1 (Tryptophan hydroxylase-1), RNA of the cell obtained in Example 1-3 was extracted using Easy-Spin™ Total RNA Extraction Kit (Intron) according to the manufacturer's method. After synthesizing cDNA from the extracted RNA using High-Capacity RNA-to-cDNA™ Kit according to the manufacturer's method, qRT-PCR (quantitative Real-time Polymerase Chain Reaction) was performed on Rotor-Gene Q (QIAGEN) with Rotorgene SYBR Green PCR kit or on Quantstudio 5 (Thermofisher) with Power SYBR Green Master Mix (Applied Biosystems).

The Tph1 expression amount was calculated as a difference of relative expression of measured values using Tph-1 F and Tph1 R primers, or Tph-1A F and Tph-1A R primers compared to the β-actin measured value with Rat B-actin F and Rat B-actin R primers, as disclosed in Table 1 (ΔΔCT analysis). The primers and temperature conditions used for qRT-PCR were summarized in following Table 1 and Table 2, respectively.

TABLE 1

| Primer | Sequence |
| --- | --- |
| Tph-1 F | ggctttgaggtcctctttcca (SEQ ID NO: 2) |
| Tph-1 R | ccccctttctgaggaatggtc (SEQ ID NO: 3) |
| Tph-1A F | accctgggatgtgcttcatg (SEQ ID NO: 4) |
| Tph-1A R | gcgttctgcaaagcaacaga (SEQ ID NO: 5) |
| Rat B-actin F | cagccttccttcctgggtatg (SEQ ID NO: 6) |
| Rat B-actin R | tagagccaccaatccacacag (SEQ ID NO: 7) |

TABLE 2

| Temperature | Time | Cycle |
| --- | --- | --- |
| 95° C. | 5 minutes | 1 cycle |
| 94° C. | 15 seconds | 50 cycles |
| 60° C. | 30 seconds | |
| 72° C. | 30 seconds | |

Figure 1:
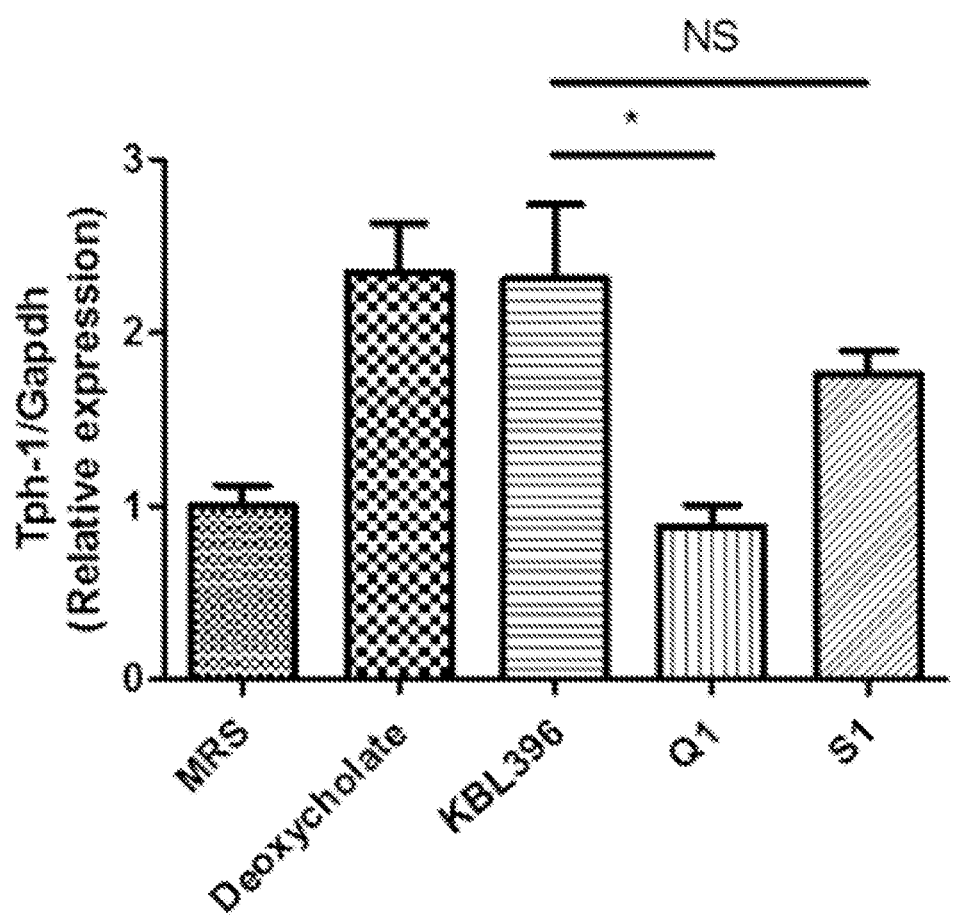

The experimental result performed under the above conditions was shown in FIG. 1.

As shown in FIG. 1A (analyzed by Rotor-Gene Q (QIAGEN) with Rotorgene SYBR Green PCR kit, Tph-1 F and Tph1 R primers), the group treated with the KBL396 strain showed Tph1 expression 2 to 4 times more at maximum compared to the group treated with other strains and group treated with 25 μM deoxycholate.

In addition, the result of comparing to commercially available *Lactobacillus plantarum* strains was shown in FIG. 1B (analyzed by Quantstudio 5 (Thermofisher) with Power SYBR Green Master Mix (Applied Biosystems), using Tph-1A F and Tph-1A R primers). As shown in FIG. 1B, it could be confirmed that the KBL396 strain, the strain of the present invention had excellent ability to induce Tph1 expression (Q1, *Lactobacillus plantarum* 299v; S1, *Lactobacillus plantarum* PS128).

Through the above result, it was confirmed that the KBL396 strain, which was the strain isolated from feces of a normal Korean adult women and the strain collected with the consent of the donor and the approval of clinical research (IRB No. 144-2011-07-11) at Samsung Seoul Hospital.

Example 2. Preparation of Feed Comprising KBL396 Strain and Feed Administration of Animal Model As it was confirmed that the KBL396 strain showed an excellent effect on serotonin biosynthesis in vitro through Example 1, in order to confirm whether the KBL396 strain shows an excellent effect on neurological diseases in vivo, an experiment using an animal model by a preclinical experiment was to be progressed, and for this, feed comprising the KBL396 strain was prepared and it was administered in the animal model.

2-1. Preparation of Feed

As oral gavage causes great stress to an experimental animal and such stress may affect the objectivity of the experimental result (bias), an experiment of administering in a form of feed prepared by mixing the strain to the animal model was planned.

The feed used for administration of the strain was prepared by the following method. The KBL396 strain was activated by culturing in an MRS medium for 24 hours, and sub-cultured for 24 hours by inoculating 1% in a new MRS medium. Then, the cell culture was centrifuged at 6000 rpm and 4° C. for 20 minutes and then the supernatant was discarded, and pellets were resuspended with 4° C. 1×PBS. Then, 1×PBS was added more than 50% of the volume of the culture supernatant to allow sufficient release. After that, it was centrifuged under the same condition as above, and washing was repeated twice, and then pellets were resuspended with 1×PBS (bacterial concentrate).

Radiation sterilized feeds were crushed into a powder forms, mixed with 'bacterial concentrate' prepared as above, and aliquoted into balls of suitable size and frozen at −80° C. for 24 hours. Then, the frozen feed-bacterial mixtures were freeze-dried for 48-72 hours and stored at −80° C. before use. The amount of the KBL396 strain contained in freeze-dried feed ('feed including the KBL396') was about 1×10$^9$ CFU/g, and the control group ('feed including PBS') was prepared by mixing PBS at a same weight of 'bacterial concetrate' as the feed prepared by mixing the strain in the same method, and stored at −80° C.

2-2. Administration of Feed

The 'feed including PBS' and 'feed including the KBL396 strain' were stored at −80° C. after preparation and were taken out every day and provided at 9 AM every day, and 3-5 g feed per one C57BL/6 mouse was supplied (the amount was increased depending on the age of week). When the feed was supplied, the remained feed was collected and the feed intake amount and strain intake amount were calculated. The animal model was observed, while administering the feed for 28 days or more.

Example 3. Effect of Cognitive Ability Improvement by KBL396 Strain Administration (Y-MAZE Experiment)

The effect of the cognitive ability improvement caused by the KBL396 treatment was tested by performing a Y-maze experiment, after administration of the strain for 28 days. The animal model used in the present invention was 7-week C57BL/6 mice, and the experiment was performed using 8 mice in the PBS control group and KBL396 treated groups, respectively.

The Y-MAZE experiment is a behavioral experiment devised for judgement of cognitive ability using the animal model. In the experiment, the three arms of the Y-maze were interconnected at 120° angle, and each arm was designated as A, B and C, and the experimental animals were placed in one arm and allowed to move freely for 8 minutes, and then the number and order of entering each arm were observed and recorded with a camera installed on the ceiling and a computer program connected to it. Then, the number and order of entering each arm were recorded when the tail completely entered, and cases of re-entering the same arm were also recorded. When entering 3 arms different each other in order (actual alteration), that is, entering in order of ABC, CAB, BAC, and the like, 1 score was given, and % alteration behavior was calculated by the following formula.

% Alteration behavior=actual alteration/maximum alternation×100(maximum alteration:total number of entries−2)

Figure 2:
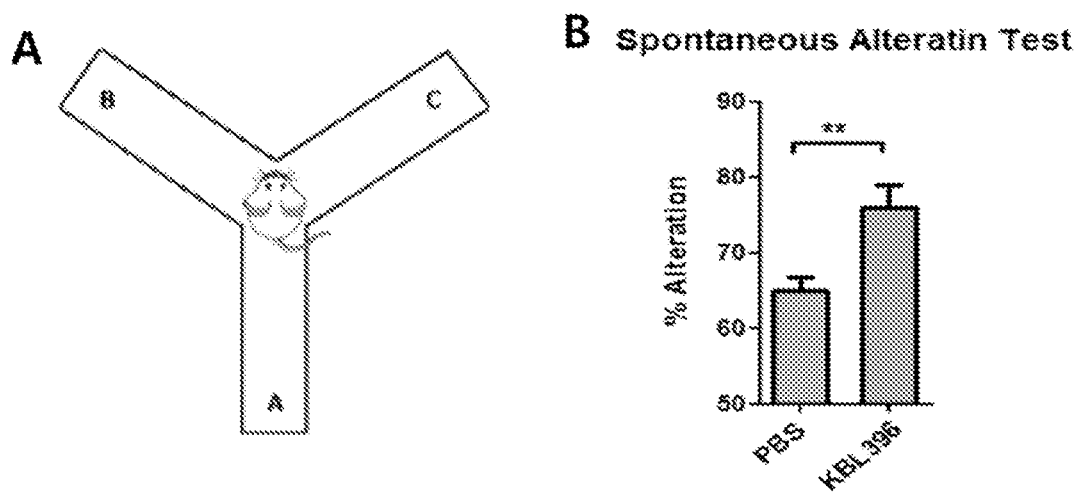
FIG. 2 is a schematic diagram of the experimental apparatus for the Y-MAZE test (A) and the result of measuring the improvement of the alteration action power of administration of the *Lactobacillus plantarum* KBL396 (KCTC13278BP) according to the Y-MAZE test (B).

The result was shown in FIG. 2. As could be seen in FIG. 2, it could be confirmed that the significantly high effect of improving the cognitive ability was shown in the animal model administered with KBL396, compared to the animal model with PBS control.

Example 4. Effect of Increasing Serotonin in Brain by KBL396 Strain Administration Whether administration of the KBL396 strain could increase serotonin in brain was tested.

At first, the amount of TPH-2 (tryptophan hydroxylase-2), a rate-limiting enzyme of the serotonin biosynthesis pathway of brain tissue, was confirmed by the amount of mRNA for that enzyme. cDNA was synthesized by extracting RNA according to the same method as Example 1-4 in the brain tissue obtained in the animal model of Example 3. In the synthesized cDNA, the expression level of Tph2 was confirmed, using Rotor-Gene Q (QIAGEN), Rotorgene SYBR Green PCR kit and the following TPH-2f, TPH-2r primers. Other experimental conditions and the analysis of the result by comparing to the Gapdh gene expression were progressed as same as Example 1-4.

TPH-2f:
(SEQ ID NO: 8)
5' CAGTCCACGAAGATTTCGACTT 3'

TPH-2r:
(SEQ ID NO: 9)
5' GCAAGACAGCGGTAGTGTTCT 3'

Figure 3:
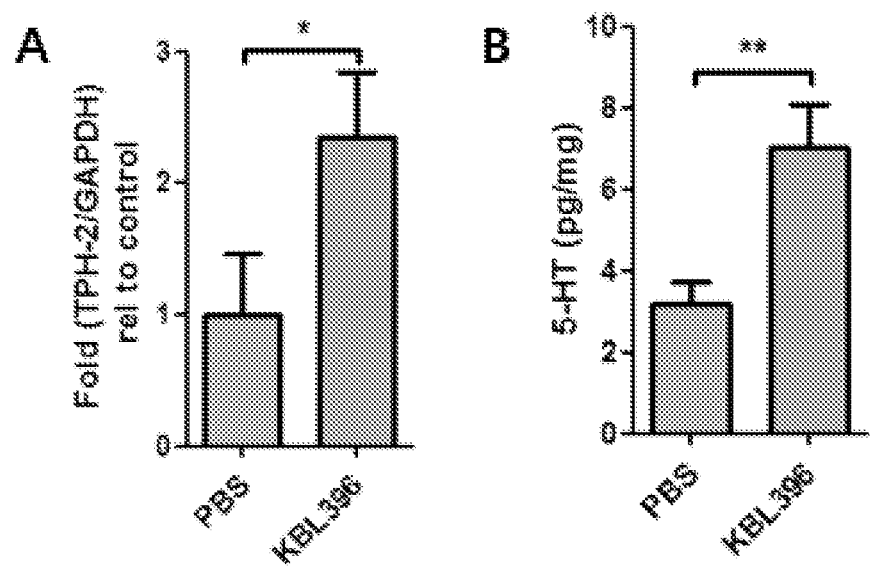
FIG. 3 shows the result of confirming the Tph2 gene expression increase and serotonin (5-HT) concentration increase by administration of the *Lactobacillus plantarum* KBL396 (KCTC13278BP) in the Y-MAZE test.

The experimental result performed under the above condition was shown in FIG. 3A. By testing that Tph2 gene was expressed significantly high in the animal model administered by KBL396 (KBL396), compared to the animal model administered by PBS (PBS), it was confirmed that serotonin biosynthesis was promoted.

Next, to directly measure the serotonin concentration of the brain tissue, enzyme-linked immunosorbent assay (ELISA) was conducted. Stainless steel bead, 5 mm (Qiagen) and T-PER™ Tissue Protein Extraction Reagent (Sigma) were added to the brain tissue obtained in the animal model of Example 3 and the tissue was lysed using Tissue lyser II (Qiagen) under the condition of 30 hz for 10 minutes. By performing centrifugation with a lysed mixture (4° C., 11,000×g, 15 minutes), an intermediate layer of aqueous layer was obtained and stored at −80° C. before use for analysis ('aqueous sample'). To measure the amount of serotonin of 'aqueous sample', by preparing samples using Serotonin Ultrasensitive ELISA Assay Kit (Eagle biosciences) according to the manufacturer's method, they were analyzed by Spark 10M Microplate Reader (Tecan).

The analysis result of the measured serotonin (5-HT) was shown in FIG. 3B. By confirming that serotonin (5-HT) at more than twice concentration was measured in the animal model in which KBL396 was administered (KBL396), compared to the animal model in which PBS control group was administered (PBS), it was confirmed that the KBL396 strain actually increased the serotonin concentration in brain.

Example 5. Effect of Improving Resilience of Stress According to KBL396 Strain Administration (Social Avoidance Test)

Social Avoidance Test is a behavior experiment to evaluate an effect on stress using an animal model. In the present invention, to confirm the effect of enhancing resistance to stress exposure of the KBL396 strain, after inducing stress to mice, the social avoidance experiment according to KBL396 strain administration was progressed.

At first, the animal model used in the present invention was 7-week C57BL/6 mice, and the experiment was performed in 4 groups of PBS control group, PBS+stress induced group, KBL396 strain treated group, KBL396 strain+stress induced group, with 8 mice in each group.

The 'feed including PBS' or 'feed including the KBL396' was administered for 4 weeks (28 days) in total and mice were exposed to stress. Even during the period of 7 days of being exposed to stress, as feed, the 'feed including PBS' or 'feed including the KBL396' was continuously provided.

Figure 4A:
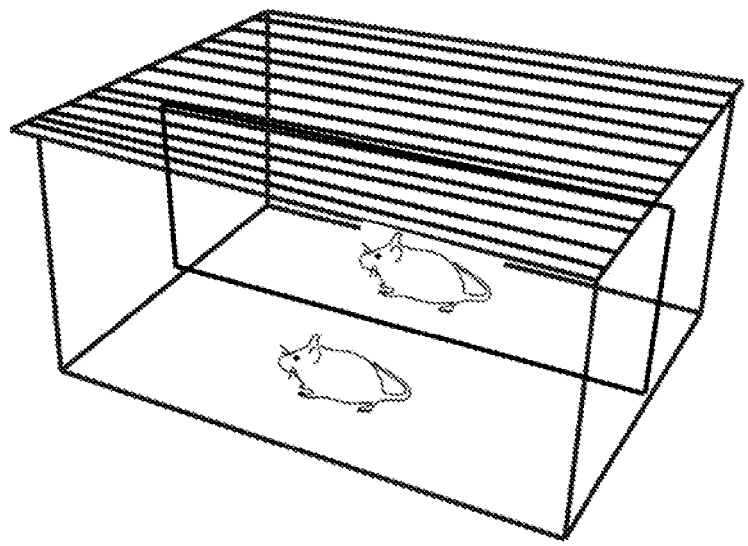
FIG. 4 is the cage for causing stress in the animal model by social defeat (A) and a schematic diagram of the experimental box for the social avoidance test (B).
Figure 4:
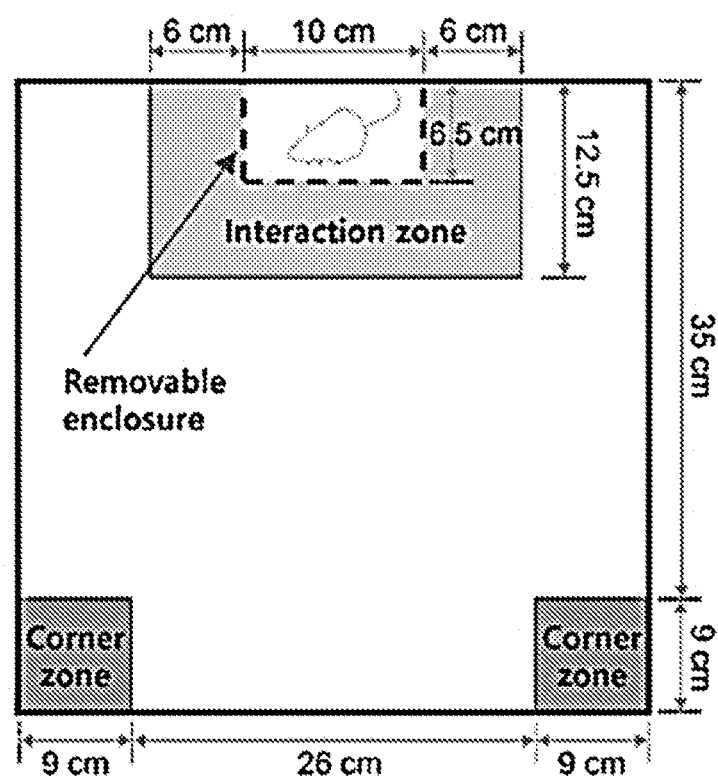

FIG. 4 is the cage for causing stress in the animal model by social defeat (A) and a schematic diagram of the experimental box for the social avoidance test (B). In order to induce stress to mice, C57BL/6 mice were made to live in the same cage with a CD-1 mouse with a transparent boundary wall made of acrylic plate with a hole in the center. During the period of 7 days, C57BL/6 mice were moved for cohebitation with the offensive CD-1 mouse once a day, and allowed to be physically attacked by the CD-1 mouse (Social defeat stress). After a total of 5 minutes of attack, C57BL/6 mouse was maintained in the cage with a transparent boundary wall for 24 hours where a new CD-1 mouse was on opposite side. Since C57BL/6 mouse was exposed to the threat of the CD-1 mouse for 24 hours and continuously recognized the presence of the aggressor CD-1 mouse, it was made to be exposed to not only physical stress but also mental stress followed during the social defeat period.

Then, to evaluate the behavior change caused by the stress exposure, the social avoidance test was performed. The social avoidance test was composed of two sets of experiments performed in the same behavior experimental box. In the first set, C57BL/6 mice were made to move freely for 3 minutes by placing them in the middle of the box. In the second set, the CD-1 mouse was placed in the removable enclosure and placed in the middle of one side of the behavior experimental box, and then the behavior of the C57BL/6 mouse was observed for 3 minutes. Then, the C57BL/6 mice exposed to social defeat stress showed the behavioral aspect of escaping to the corner zone and staying still when they confirmed the presence of the CD-1 mouse, and the period of time that C57BL/6 stayed in the corner zone was measured to determine the degree of social avoidance.

Figure 5:
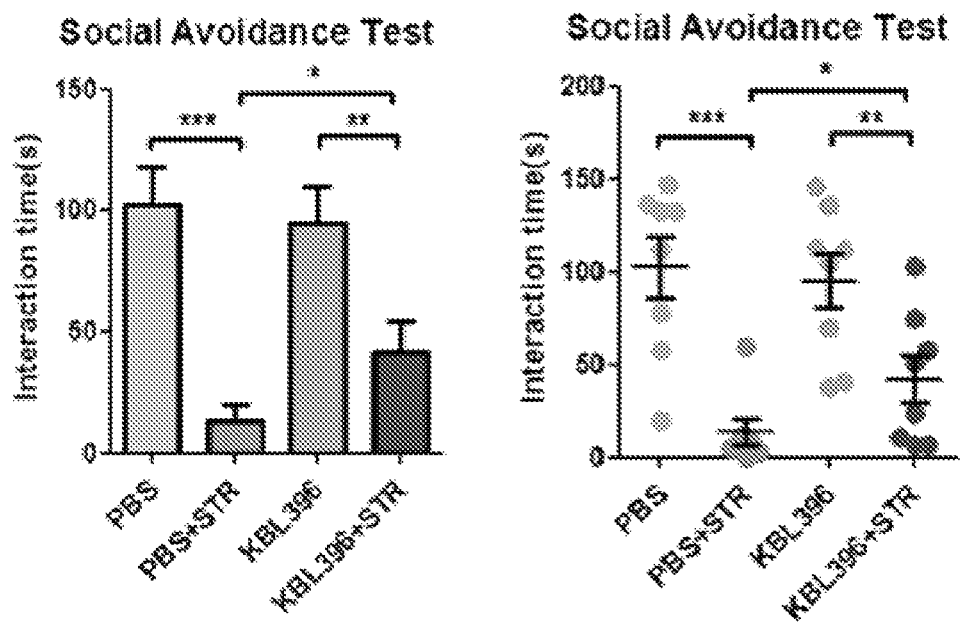
FIG. 5 is the result of confirming the effect of improving the resilience of stress induced by social defeat when administering the *Lactobacillus plantarum* KBL396 (KCTC13278BP) to a C57BL/6 mouse.

The result was shown in FIG. 5. As could be seen in FIG. 5, it could be confirmed that the degree of social avoidance was significantly improved, when the social attack stress was induced in mice in which KBL396 of the present invention was administered (KBL396+STR).

Example 6. Effect of Improving Depression by KBL396 Strain Administration (Tail Suspension Test)

The C57BL/6 mice suffering social attack stress in Example 5 showed a depressive-like behavior, which is a well-known mouse model of depression research area. In the present invention, to confirm the effect of attenuating effect of depression by administration of the KBL396, a tail suspension test was carried out with the C57BL/6 mice from social attack stress.

The administration of KBL396 and induction of depression by stress exposure were performed similarly to the method of Example 5, and KBL396 was administered the same during receiving the social attack stress.

In a separated area, the tail of C57BL/6 mouse suffered from social attack stress was attached to the ceiling with sticky tape, which clung to about 1 cm from the tail end, and the immobile time was measured during last 4 minutes out of 6 minutes of total experimental time. The immobile state means the state in which any movement from the suspended state is completely stopped.

Figure 6:
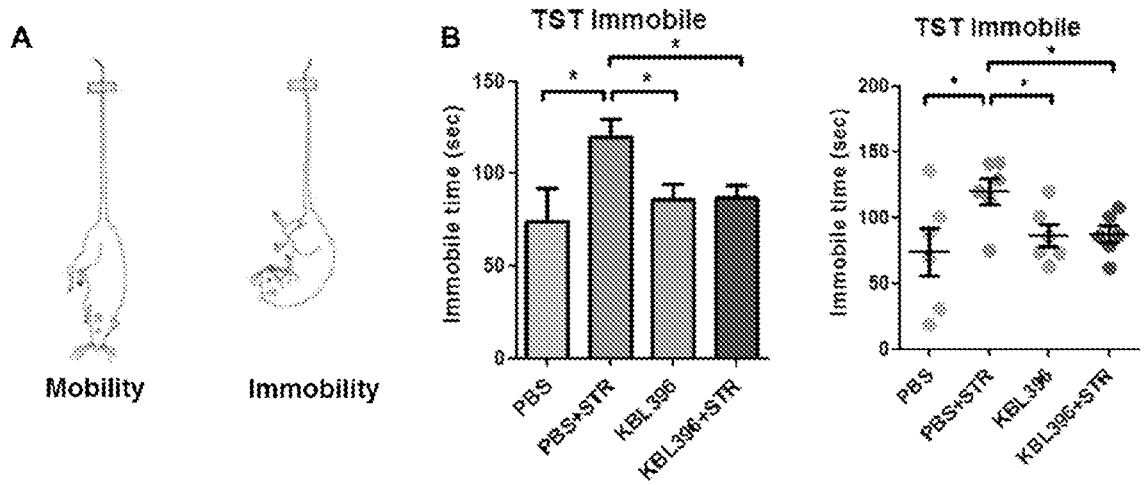
FIG. 6 is a schematic diagram showing the method of the tail suspension experiment (A) and the result of confirming the resilience for stress induced by social defeat when administering the *Lactobacillus plantarum* KBL396 (KCTC13278BP) to a C57BL/6 mouse by the tail suspension experiment (B).

The result of the tail suspension test was shown in FIG. 6. As shown in FIG. 6, it could be confirmed that in the KBL396 administered group (KBL396+STR), compared to the control group in which depression was induced (PBS+STR), depression phenotype was restored at the same level in the normal control group, although it was exposed to the same stress.

From the above result, it can be seen that administration of the KBL396 strain has an effect of improving the cognitive ability and an effect of prevention and treatment of depression by stress.

Example 7. Effect of Regulating Inflammatory Reaction of Brain According to KBL396 Strain Administration To confirm the effect of regulating the inflammatory reaction of brain according to KBL396 strain administration, the amount of IL-1β, the inflammatory cytokine was confirmed by extracting the total protein of the brain tissue obtained in the animal model of Example 5 and performing ELISA. In the brain tissue of the animal model of Example 5, by the same process as Example 4, 'aqueous sample' was obtained. The measurement of the protein concentration of the 'aqueous sample' was progressed using BCA Protein Assay Kit (Pierce, USA) according to the manufacturer's method. To measure the amount of IL-1β, samples were prepared using Mouse IL-1β ELISA kit (Sigma Aldrich) according to the manufacturer's method, and analyzed by the same process as Example 4.

Figure 7:
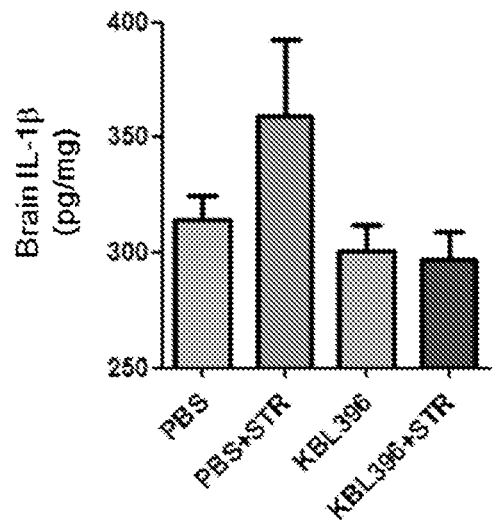
FIG. 7 is the result of confirming the change of the expression of the IL-1B that is the inflammatory cytokine, when administering the *Lactobacillus plantarum* KBL396 (KCTC13278BP), in the brain of the animal model for the social avoidance test.

The analysis result of IL-1β measured was shown in FIG. 7. The concentration of IL-1β, one of the inflammatory cytokines, was increased in the brain of the mouse in which depression was induced (PBS+STR), compared to the brain of the normal mouse (PBS), but in the brain of the KBL396 administered group (KBL396 and KBL396+STR), the concentration of IL-1β was maintained at a similar level to the normal control group regardless of stress exposure.

Example 8. Effect of Regulating Stress-Induced Immune Imbalance by KBL396 Strain Administration CD4+ T cell and CD8+ T cell are recognized to contribute to anti-inflammation and promotion of inflammation, respectively, and the reduction of the CD4/CD8 T cell ratio that is the relative ratio of them causes reduction of inflammation resistance and immune imbalance such as immune aging. In addition, regulatory T cells (Treg) are responsible for immune regulation to prevent excessive reactions of the immune system. When the imbalance of immune regulated by T cells was caused as above, inflammatory reactions are shown, and in particular, the inflammatory reaction in nerves and brain are highly likely to cause degenerative brain diseases such as dementia and depression, and the like. To confirm how the KBL396 treatment affects T cells involved in immune regulation, flow cytometry (Fluorescence-activated cell sorting, FACS) was performed with the spleen tissue and mesenteric lymph node cells of the mice of Example 5.

The tissue was stored in RPMI1640 medium containing 10% inactivated FBS on ice when sacrificed. To prevent loss of cells, the tissue was sampled right after sacrifice, followed by filtering through a 70 μm cell strainer to obtain single cells, and then stained by trypan blue and the number of live cells was counted. Then, about $1 \times 10^7$ cells were moved to a 96 well, and a fluorescent antibody targeting each immune marker was attached. The immune marker used herein were FITC-conjugated anti-mouse CD3, PerCP-Cy5.5-conjugated anti-mouse CD4, PE-conjugated anti-mouse CD8, PE-conjugated anti-mouse FOXP3, APC-conjugated anti-mouse CD25 monoclonal antibodies (all eBioscience), respectively. Then, flow cytometry was performed by BD FACSVerse™ (BD bioscience), and immunocytes were identified using Flowjo software (BD bioscience).

Figure 8:
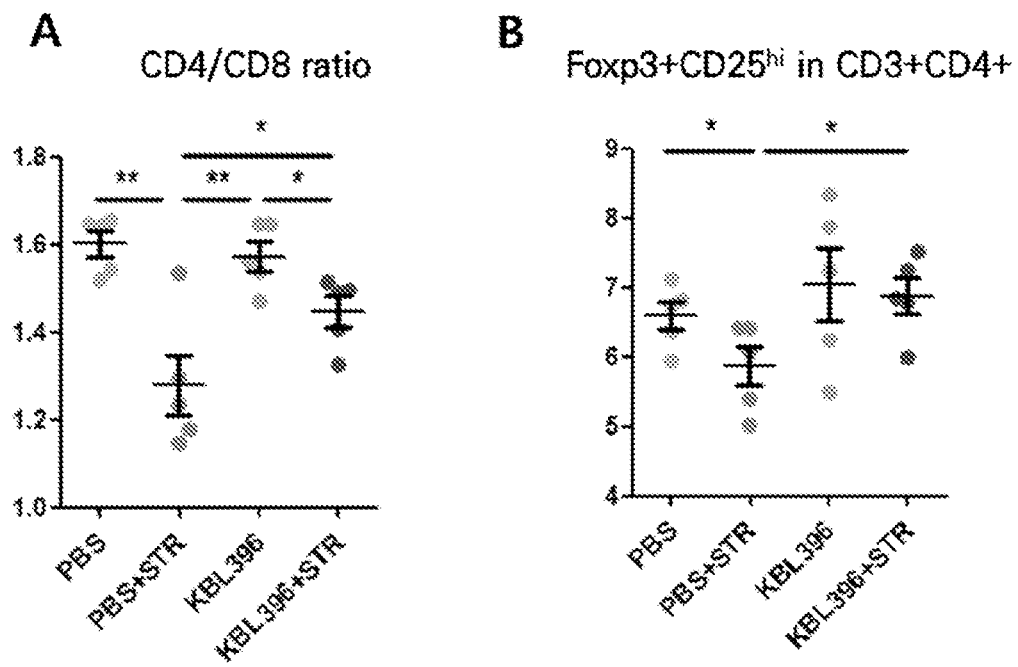
FIG. 8 is the result of confirming the CD4/CD8 ratio change and the change of FOXP3+CD25 cell in CD3+CD4+ in the spleen when administering the *Lactobacillus plantarum* KBL396 (KCTC13278BP) in the animal model for the social avoidance test.

The flow cytometry results were shown in FIG. 8. The mice exposed to stress (PBS+STR) were prone to inflammation as the CD4/CD8 T cell ratios of the spleen tissues were reduced compared to those of the normal mice (PBS), but when the KBL396 cells were administered (KBL396+STR), the ratios were restored significantly (FIG. 8A). In addition, the amounts of Treg cells of mesenteric lymph nodes were also reduced according to stress exposure (PBS+STR), but when the KBL396 cells were administered (KBL396+STR), they were significantly recovered similar to those of the unstressed mice (FIG. 8B). Accordingly, it was confirmed that the immune imbalance caused by stress exposure could be alleviated by KBL396 administration.

Example 9. Confirmation of Carbon Source Availability and Enzyme Activity of KBL396 Strain The carbon source availability of physiological properties of the *Lactobacillus plantarum* KBL396 (KCTC13278BP) was analyzed by a sugar fermentation test with API Kit (model name: API 50 CHL; manufacturer: BioMerieux's, USA), and the result was shown in the following Table 3. In the following Table 3, "+" shows the case in that the carbon source availability is positive.

In addition, the enzyme activities, one of physiological properties of the *Lactobacillus plantarum* KBL396 (KCTC13278BP) were analyzed by an enzyme activity experiment with API Kit (model name: API-ZYM CHL; manufacturer: BioMerieux's, USA), and the result was shown in the following Table 4. In the following Table 4, "+" shows the case in that there is enzyme activity.

TABLE 3

| Strip No. | Abbr.[1] | Substrate (Full name) | L. plantarum KBL 396 |
|---|---|---|---|
| 5 | RIB | D-Ribose | + |
| 10 | GAL | D-Galactose | + |
| 11 | GLU | D-Glucose | + |
| 12 | FRU | D-Fructose | + |
| 13 | MNE | D-Mannose | + |
| 18 | MAN | Mannitol | + |
| 19 | SOR | Sorbitol | + |
| 20 | MDM | α-Methyl-D-Mannoside | + |
| 21 | MDG | α-Methyl-D-Glucoside | + |
| 22 | NAG | N-Acethyl-Glucosamine | + |
| 23 | AMY | Amygdalin | + |
| 24 | ARB | Arbutin | + |
| 25 | ESC | Esculin | + |
| 26 | SAL | Salicin | + |
| 27 | CEL | Celiobiose | + |
| 28 | MAL | Maltose | + |
| 29 | LAC | Lactose | + |
| 30 | MEL | Melibiose | + |
| 31 | SAC | Sucrose | + |
| 32 | TRE | Trehalose | + |
| 34 | MLZ | Melezitose | + |
| 39 | GEN | Gentiobiose | + |

TABLE 4

| No. | Enzyme Assayed For | L. plantarum KBL 396 |
|---|---|---|
| 1 | Control | − |
| 2 | Alkaline phosphatase | − |
| 3 | Esterase (C4) | − |
| 4 | Esterase Lipase (C8) | − |
| 5 | Lipase (C14) | − |
| 6 | Leucine arylamidase | + |
| 7 | Valine arylamidase | + |
| 8 | Crystine arylamidase | − |
| 9 | Trypsin | − |
| 10 | α-chymotrypsin | − |
| 11 | Acid phosphatase | − |
| 12 | Naphtol-AS-BI-phosphohydrolase | − |
| 13 | α-galactosidase | − |
| 14 | β-glucuronidase | − |
| 15 | β-glucosidase | − |
| 16 | α-glucosidase | + |
| 17 | β-glucosidase | + |
| 18 | N-acetyl-β-glucosaminidase | − |
| 19 | α-mannosidase | − |
| 20 | α-fucosidase | − |

Example 10. Formulation of KBL396 Strain

After KBL396 strain obtained from an operation of a fermenter was harvested by a centrifuge, the supernatant of medium remained was discarded and washed with 1×PBS (phosphate buffer saline) to remove residues of the medium. As a stable formulation for cryoprotective agent (CPA), it was treated with skimmed milk, sucrose and sorbitol (skim milk 11%+sucrose 4.29%+sorbitol 5.69% based on the total weight of the formulation), and 1×PBS was treated as a negative control group to progress freeze-drying. The strain harvested by the centrifuge was concentrated to 20 times of the removed supernatant and the cryoprotectant (CPA) was treated, and after freezing at −80° C. for 24 hours overnight, for the completed strain, the fine grinding was carried out twice and the viability was measured. The viability of freeze-drying was calculated from the CFU counting result before freezing and after freeze-drying.

Figure 9:
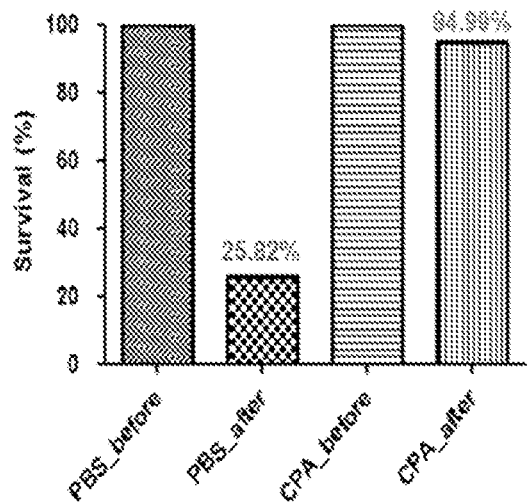
FIG. 9 is the result of confirming the change of the viability according to freeze-drying by treating a cryoprotectant to the *Lactobacillus plantarum* KBL396 (KCTC13278BP).

As a result, as FIG. 9, while the viability of 25.8% was shown as the result of treating 1×PBS, the viability of 95% was shown when treating CPA, and thereby the definite increase effect of the viability according to freeze-drying could be confirmed.

Deposition Information of *Lactobacillus plantarum* KBL396 (KCTC13278BP)

The inventors of the present invention deposited the *Lactobacillus plantarum* KBL396 (KCTC13278BP) to Korean Collection for Type Culture, the authorized depository institution on May 29, 2017 (address: Korea Research Institute of Bioscience and Biotechnology, 181 Inspin-gil, Jeongeup-si, Jeollabuk-do, 56212, Korea) and received the accession number of KCTC13278BP.

The strain has been deposited under conditions that assure that access to the culture will be available during pendency of the patent application and for a period of 30 years, or 5 years after the most recent request, or for the effective life of the patent, whichever is longer.

As above, the present invention has been described by the above examples, but the present invention is not necessarily limited thereto, and various modifications can be made without departing from the scope and spirit of the present invention. Accordingly, the scope of the present invention should be construed to include all embodiments falling within the scope of the claims appended to the present invention.

INDUSTRIAL APPLICABILITY

The *Lactobacillus plantarum* KBL396 (KCTC13278BP), culture of the strain, lysate of the strain and extract of the strain according to the present invention exhibit an excellent effect on improvement of neurological diseases without risk of side effects of conventional therapeutic agents used for neurological diseases, in addition to advantages of being safe and non-toxic in a human body and easily accessible without negative recognition as a therapeutic agent, and therefore it may be very usefully used industrially.

The invention claimed is:

1. A method for treating a mental disorder by increasing serotonin, comprising administering a composition comprising at least one selected from the group consisting of a Lactobacillus plantarum KBL396 strain (KCTC13278BP), culture of the strain, lysate of the strain and extract of the strain, to a subject in need thereof a therapeutically effective amount, wherein administration of said composition results in increased levels of serotonin in the subject to which the composition is administered.

2. The method according to claim 1, wherein the mental disorder is at least one selected from the group consisting of stress-induced tension, anxiety, depression, mood disorder, insomnia, delusional disorder, obsessive compulsive disorder, migraine, memory disorder, cognitive disorder and attention disorder.

3. The method according to claim 1, wherein the composition further comprises at least one of pharmaceutically acceptable excipients and/or freeze-drying agents.

4. A method for treating a neurodegenerative disease by increasing serotonin, comprising
administering a composition comprising at least one selected from the group consisting of a Lactobacillus plantarum KBL396 strain (KCTC13278BP), culture of the strain, lysate of the strain and extract of the strain, to a subject in need thereof a therapeutically effective amount,
wherein the neurodegenerative disease is at least one selected from the group consisting of Parkinson's disease, Huntington's disease, Alzheimer's disease, amyotrophic lateral sclerosis, Tourette's syndrome, Friedrich's ataxia, dementia and dystonia, wherein administration of said composition results in increased levels of serotonin in the subject to which the composition is administered.

5. The method according to claim 4, wherein the composition further comprises at least one of pharmaceutically acceptable excipients and/or freeze-drying agents.

6. A method for increasing serotonin comprising administering a therapeutically effective amount of composition comprising at least one selected from the group consisting of a Lactobacillus plantarum KBL396 strain (KCTC13278BP), culture of the strain, lysate of the strain and extract of the strain to a subject in need thereof.

* * * * *

SEQUENCE LISTING

<160> NUMBER OF SEQ ID NOS: 9

<210> SEQ ID NO 1
<211> LENGTH: 1492
<212> TYPE: DNA
<213> ORGANISM: Lactobacillus plantarum

<400> SEQUENCE: 1

```
tatcagtacg tgctataatg cagtcgacga ctctggtatt gattggtgct tgcatcatga    60
tttacatttg agtgagtggc gaactggtga gtaacacgtg ggaaacctgc ccagaagcgg   120
gggataacac ctggaaacag atgctaatac cgcataacaa cttggaccgc atggtccgag   180
cttgaaagat ggcttcggct atcacttttg gatggtcccg cggcgtatta gctagatggt   240
ggggtaacgg ctcaccatgg caatgatacg tagccgacct gagagggtaa tcggccacat   300
tgggactgag acacggccca aactcctacg ggaggcagca gtagggaatc ttccacaatg   360
gacgaaagtc tgatggagca acgccgcgtg agtgaagaag ggtttcggct cgtaaaactc   420
tgttgttaaa gaagaacata tctgagagta actgttcagg tattgacggt atttaaccag   480
aaagccacgg ctaactacgt gccagcagcc gcggtaatac gtaggtggca agcgttgtcc   540
ggatttattg ggcgtaaagc gagcgcaggc ggttttttaa gtctgatgtg aaagccttcg   600
gctcaaccga agaagtgcat cggaaactgg gaaacttgag tgcagaagag acagtggaa   660
ctccatgtgt agcggtgaaa tgcgtagata tatggaagaa caccagtggc gaaggcggct   720
gtctggtctg taactgacgc tgaggctcga agtatgggt agcaaacagg attagatacc   780
ctggtagtcc ataccgtaaa cgatgaatgc taagtgttgg agggtttccg cccttcagtg   840
ctgcagctaa cgcattaagc attccgcctg gggagtacg gcccgcaagg ctgaaactca   900
aaggaattga cggggggccc gcacaagcgg tgggagcatg tgggtttaat tcaaagctac   960
gcgaagaaac cttacccagg ttttgacata ctaatgcaaa ttctaaagag attagaacgt  1020
ttcccttccg gggacatggg ataccggtg ggtgcatggg ttggtcgtca gcttcgtggt  1080
cgtgagaatg tttgggttta agttccccga aacgagcgca acccttatta tcagttgcca  1140
gcattaagtt gggcactctg gtgagactgc cggtgacaaa ccggaggaag gtggggatga  1200
cgtcaaatca tcatgcccct tatgacctgg gctacacacg tgctacaatg gatggtacaa  1260
cgagttgcga actcgcgaga gtaagctaat ctcttaaagc cattctcagt tcggattgta  1320
ggctgcaact cgcctacatg aagtcggaat cgctagtaat cgcggatcag catgccgcgg  1380
tgaatacgtt cccgggcctt gtacacaccg cccgtcacac catgagagtt tgtaacaccc  1440
aaagtcggtg ggtaacctt tagaaccagc cgcctaatgg caccaccatg cg           1492
```

<210> SEQ ID NO 2
<211> LENGTH: 21
<212> TYPE: DNA
<213> ORGANISM: Artificial Sequence
<220> FEATURE:
<223> OTHER INFORMATION: Tph-1 F Primer

<400> SEQUENCE: 2

```
ggctttgagg tcctctttcc a                                              21
```

<210> SEQ ID NO 3
<211> LENGTH: 21
<212> TYPE: DNA
<213> ORGANISM: Artificial Sequence
<220> FEATURE:
<223> OTHER INFORMATION: Tph-1 R Primer

<400> SEQUENCE: 3

```
cccccttctt gaggaatggt c                                              21
```

<210> SEQ ID NO 4

```
<211> LENGTH: 20
<212> TYPE: DNA
<213> ORGANISM: Artificial Sequence
<220> FEATURE:
<223> OTHER INFORMATION: Tph-1A F Primer

<400> SEQUENCE: 4
accctgggat gtgcttcatg                                              20

<210> SEQ ID NO 5
<211> LENGTH: 20
<212> TYPE: DNA
<213> ORGANISM: Artificial Sequence
<220> FEATURE:
<223> OTHER INFORMATION: Tph-1A R Primer

<400> SEQUENCE: 5
gcgttctgca aagcaacaga                                              20

<210> SEQ ID NO 6
<211> LENGTH: 21
<212> TYPE: DNA
<213> ORGANISM: Artificial Sequence
<220> FEATURE:
<223> OTHER INFORMATION: Rat B-actin F Primer

<400> SEQUENCE: 6
cagccttcct tcctgggtat g                                            21

<210> SEQ ID NO 7
<211> LENGTH: 21
<212> TYPE: DNA
<213> ORGANISM: Artificial Sequence
<220> FEATURE:
<223> OTHER INFORMATION: Rat B-actin R Primer

<400> SEQUENCE: 7
tagagccacc aatccacaca g                                            21

<210> SEQ ID NO 8
<211> LENGTH: 22
<212> TYPE: DNA
<213> ORGANISM: Artificial Sequence
<220> FEATURE:
<223> OTHER INFORMATION: TPH-2f Primer

<400> SEQUENCE: 8
cagtccacga agatttcgac tt                                           22

<210> SEQ ID NO 9
<211> LENGTH: 21
<212> TYPE: DNA
<213> ORGANISM: Artificial Sequence
<220> FEATURE:
<223> OTHER INFORMATION: TPH-2r Primer

<400> SEQUENCE: 9
gcaagacagc ggtagtgttc t                                            21
```